United States Patent
Pitz et al.

(10) Patent No.: US 8,369,694 B2
(45) Date of Patent: Feb. 5, 2013

(54) PORTABLE VAPORIZING DISPENSER

(75) Inventors: Kevin J. Pitz, Ruskin, FL (US); Michael Sheppard Bolmer, Sarasota, FL (US); Zbigniew R. Paul, University Park, FL (US); Cullen M. Sabin, Bradenton, FL (US); Martin W. Sabin, Sarasota, FL (US)

(73) Assignee: Tempra Technology, Inc., Bradenton, FL (US)

( * ) Notice: Subject to any disclaimer, the term of this patent is extended or adjusted under 35 U.S.C. 154(b) by 735 days.

(21) Appl. No.: 11/995,175

(22) PCT Filed: Jul. 31, 2006

(86) PCT No.: PCT/US2006/030572
§ 371 (c)(1),
(2), (4) Date: May 6, 2010

(87) PCT Pub. No.: WO2007/016705
PCT Pub. Date: Feb. 8, 2007

(65) Prior Publication Data
US 2010/0260491 A1    Oct. 14, 2010

Related U.S. Application Data

(60) Provisional application No. 60/704,573, filed on Aug. 1, 2005.

(51) Int. Cl.
*F24F 6/00* (2006.01)
*A01N 25/00* (2006.01)

(52) U.S. Cl. ........ 392/390; 392/391; 392/392; 392/393; 392/394; 392/395; 219/201; 219/236; 219/537; 219/542; 219/544; 422/125; 424/40

(58) Field of Classification Search .......... 390/390–395, 390/397–8, 386, 410; 219/201, 536–7, 542, 219/544; 424/40; 422/125
See application file for complete search history.

(56) References Cited

U.S. PATENT DOCUMENTS

| | | | | |
|---|---|---|---|---|
| 4,780,286 A | * | 10/1988 | Parent et al. | 422/126 |
| 6,099,556 A | * | 8/2000 | Usui | 607/114 |
| 6,293,474 B1 | * | 9/2001 | Helf et al. | 239/102.2 |
| 6,581,915 B2 | * | 6/2003 | Bartsch et al. | 261/26 |
| 7,081,211 B2 | * | 7/2006 | Li et al. | 252/70 |

* cited by examiner

*Primary Examiner* — Shawntina Fuqua
(74) *Attorney, Agent, or Firm* — Fish & Richardson P.C.

(57) ABSTRACT

A vaporizing dispenser comprising a user-activatable chemical reaction heat source and a volatile compound inside a container such that convection currents from the activated heat source volatilize the volatile compound and carry it out of the container.

18 Claims, 5 Drawing Sheets

PORTABLE VAPORIZING DISPENSER

CROSS REFERENCE TO RELATED APPLICATIONS

This application is a national phase filing under 35 U.S.C. §371 of international application number PCT/US2006/030572, filed Jul. 31, 2006, which claims the benefit of U.S. Provisional Application No. 60/704,573, filed Aug. 1, 2005. The entire content of the prior applications is incorporated herein by reference in its entirety.

TECHNICAL FIELD

This invention relates to dispensing volatile compositions such as air fresheners, aromatherapy compounds, and insect repellants, into the air.

BACKGROUND

Evaporation of volatile liquid compositions having utility in a gaseous state is well known for numerous purposes, including air fresheners, aromatherapy, and repelling insects. Dispensers for volatile compositions may be as simple as an open container or may include dispensing aids. Dispensing aids may be passive, such as an exposed wick, to increase surface area for evaporation. They may be mechanical, such as an aerosol can dispenser or a fan. They may include heating a volatile liquid, with heat being generated by burning a candle, utilizing a butane flame, or utilizing a resistance heater powered by electricity, either a battery or household electric current. Heated dispensers suffer from one or more drawbacks of safety (flame), weight (battery or extension cord) or limited location of use (household electric current).

An aspect of this invention is a portable dispenser that generates heat to aid evaporation and dispersion of a volatile compound or compounds over an extended time, at least one hour, and preferably several hours, without flame or electric current.

Another aspect of this invention is a convection-driven vaporizing dispenser comprising a closed, insulated container having a bottom air inlet and a top air outlet, said container including therein confined solid or liquid reactants capable of producing a long-lasting, low-temperature exothermic chemical reaction when mixed with each other or exposed to air, and a volatile composition heatable by said reaction, and user-operable or user-compromisable means for preventing premature activation of the reaction ingredients.

SUMMARY

This invention is a portable dispenser for volatile liquid or solid compounds. The dispenser includes a mechanically activatable, long-lasting, low-temperature chemical convection heater and a volatile compound or compounds to be dispensed. A user activates the dispenser mechanically so as to initiate heating, which causes convective airflow upwardly through the dispenser. Air is drawn into the bottom of the dispenser, passed near or through the ingredient or ingredients of the chemical heater and also over volatile compound or compounds. The heated air exits at the top of the dispenser, carrying with it a desired concentration of evaporated volatile compound or compounds.

The dispenser may comprise a single container. A single container dispenser may have an outer wall that is insulating or insulated. Alternatively the dispenser may comprise an inner container and an outer container wherein either container or the two in combination may provide insulation. The single container, or in alternative embodiments the inner container, contains a single-use chemical reaction heater and the volatile compound or compounds to be dispensed. It includes at least one lower air intake and at least one upper air discharge opening, thereby permitting convective airflow upwardly through that container. The dispenser or its associated packaging physically separates the heat-producing reactants until a user activates the heater by mechanically compromising the physical separation. We refer to all such embodiments as having physical separation means associated with the dispenser. If a physical separation is included in the dispenser itself, the mechanical activation means form part of the dispenser. If the chemical reaction is between two ingredients included in the heater at least one is a liquid (liquid compound, solution or dispersion), for example a fuel such as glycerin and a permanganate oxidizer or calcium oxide and water, the reactants are provided in separate compartments, and the mechanical activation means is a device that when operated by the user, compromises the separation and permits the separately contained ingredients to mix and thereby react. A valve, a pouch-puncturing prong and offset but alignable holes are examples of user-operable mechanical activators that may be included as part of a single container or an inner container. Certain embodiments of chemical heaters useful in dispensers of this invention utilize air to supply oxygen, a reactant, and are initiated by admitting air to a single container or an inner container. For such embodiments the single container or inner container may be provided with covered air-inlet and air-discharge ports that can be opened by the user to compromise the separation and initiate the chemical reaction as well as to open an air passageway for dispensing volatile compound. Alternatively a single container may include open air intakes and discharges for the air passageway or for both the air passageway and oxygen reactant but be packaged in an airtight shipping or display package that a user opens, in which case mechanically compromising the separation of reactants is opening the shipping package associated with the dispenser and removing the dispenser for use.

Two-container embodiments provide the opportunity to reuse the outer container with a series of inner containers, or "refills".

A single container or inner container includes a passageway, either a single passage or multiple passages for air to flow convectively from the intake to the discharge, and a volatile compound or compounds to be contacted by flowing air during operation. Preferably the volatile compound or compounds are placed so as to be contacted by air that has been heated partially or completely, thereby increasing the evaporation rate.

The dispenser's chemical reaction heater is in thermal contact with the air passageway so as to heat air therein. Air in the passageway may contact the reacting ingredients of the heater. Alternatively, air in the passageway may be physically separated from the reacting ingredients by a heat-conducting separator.

Where needed or desired, particularly in embodiments having the chemical reaction heater proximate the exterior wall or walls of the first container rather than inside the air passageway, the dispenser includes insulation to protect a user, to reduce heat loss, or both. A single container may include an insulation layer on either the inside or outside, at least of the container's outer vertical wall or walls. Insulation may be provided by the wall (or walls) itself by making it sufficiently insulating by selection of material, construction and thickness. An air gap between the heater chamber, if separate, and the container's wall (or walls) may act as an insulating layer in appropriate constructions, as will be discussed. A layer of insulating material may be provided, for example, a paper, cardboard or plastic (preferably foamed plastic) inner or outer liner. If needed, the top may be insulated, but a user may be protected from coming into contact with a hot top by physically obstructing contact with an insulating, as opposed to a metallic, obstruction.

Two-container embodiments may include insulation associated with the inner or outer container, either container may be an insulating, or an insulating layer may be provided between the containers. An annular gap between the inner container and the outer container may comprise some or all of the insulation that is needed, particularly if at least one container's wall is non-metallic.

The dispenser may be adapted to be worn, hung, or placed on a horizontal or vertical surface by inclusion of a stand or legs, by inclusion of a strap or eyelet for a strap, by inclusion of a hook or by inclusion of means for releasable attachment to a vertical surface.

The heater ingredients and the volatile compound or compounds are in solid or liquid form. If volatile compound or compounds are liquids, they are combined with a solid object as by coating, absorption, or adsorption so as to be held in the solid object.

The heater generates heat by an exothermic reaction, commonly either oxidation or hydrolysis. We intend the term "chemical reaction heater" to be understood in its broadest sense of contacting one component, solid or liquid, with a fluid component, liquid or gas (air), whereupon heat is generated. Selection of the type of exothermic reaction and of the particular ingredients to be used is within the skill of the art, utilizing a few criteria. The exothermic reaction in the dispenser must be slow so as to persist for at least several minutes, for example 3, 5 or 10 minutes. For particular uses, for example, repelling insects, the exothermic reaction should persist for at least one hour, preferably for at least 2 hours and, for some embodiments at least as long as 12 hours. Temperature rise due to the exothermic reaction should be relatively low so as not to compromise the parts of the dispenser, overheat volatile compounds, or present safety hazards to users and surroundings. Temperatures within the dispenser should not reach 100° C., preferably not more than 70° C. The temperature of the air exiting the dispenser should not exceed about 50° C. or, if the dispenser is to be worn by a person, about 40° C. Our preferred heating compositions include iron powder and carbon powder and/or vermiculite as a solid reactant and oxygen from air as a fluid reactant. Oxidation of iron is the exothermic reaction. We refer to this as an "iron oxide" heater. An alternative is one in which water, a fluid reactant, is added to solid calcium oxide particles, referred to in the art as a "calcium oxide" heater. Still another could be the crystallization of a subcooled liquid phase, such as sodium acetate trihydrate. Yet another alternative is addition of a water solution of glycerin (fuel) to a bed of inert solid material containing particles of potassium permanganate (oxidizer) or to liquid sodium permanganate.

The performance of a heater can be tailored to a specific application by adjusting certain design parameters. The rate of evaporation of the volatile compound or compounds can be adjusted for a dispenser by changing the temperature of the heater, as higher temperature equates to a higher evaporation rate. A heater's temperature can be raised by increasing the amount of heat-producing reactant or increasing the amount of insulation, or both. A heater's temperature can be lowered by changing the foregoing parameters oppositely. Some increase can also be achieved by adjusting the air flow rate or by increasing the surface area of thermal contact between the reaction and the air. Further refinement can be achieved by passing air across the volatile compound after it has been partially heated and then further heating the air before it exits the dispenser. Larger convective air flow for a particular dispenser can be achieved by increasing the size of the entry and exit ports. Larger air flow can be utilized to reduce the concentration of volatilized compound or compounds in the air exiting the heater. If controlling, the pressure drop for air passing through the heater can be reduced by increasing the free area of the passageway for air flow through the heating ingredients and solid material comprising volatile compounds. Opposite changes can be made to reduce air flow.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
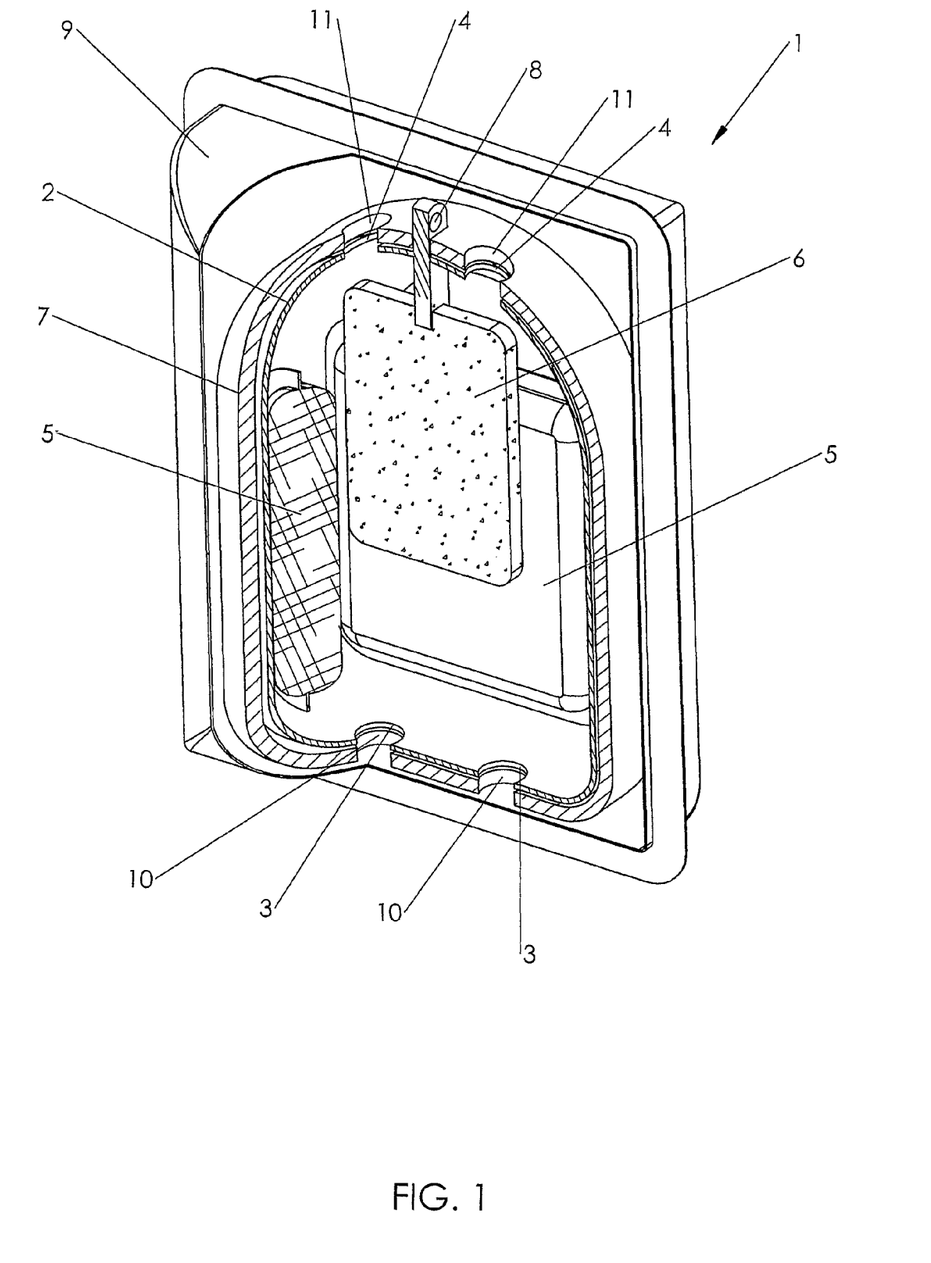
FIG. 1 is a cross-sectional view of an embodiment of a dispenser according to this invention that is suitable for wearing by a person.

FIG. 1 depicts in cross section an embodiment of a convection-driven dispenser according to this invention. The embodiment depicted in FIG. 1 includes an air-activated heater, an iron oxide heater. Dispenser 1 includes inner container 2, a closed container having bottom ports 3 and top ports 4, all of which are holes. In operation air enters bottom ports 3 and exits top ports 4. As shown, the ports are vertically oriented, but they alternatively could be horizontally oriented at the bottom and top of the container sides, respectively. Inner container 2 contains porous paper or plastic packs 5, each containing heat-reaction ingredients capable of undergoing an exothermic chemical reaction. Packs 5 confine the solid reactants. As stated earlier, we sometimes refer to the confined reaction zone as the "heater." Packs 5 in this embodiment define an air passageway extending vertically through the center of the heater from bottom ports 3 to top ports 4. Placed between packs 5, proximate the tops of the packs and projecting above the packs in the air passageway are solid volatile compounds, liquid volatile compounds held in a porous matrix. The volatile compounds are item 6. Surrounding inner container 2 is insulating outer container 7, having holes 10 aligning with ports 3 and having holes 11 aligning with ports 4. Attached to the top of package 7 is an eyelet 8 suitable for attaching a hook, chain or string for suspending dispenser 1 upright, for example, from the neck of a person. Outer container 7 is integral with inner container 2 and is optional, as a single container could provide all functions, with an insulation surround if needed.

Shipping and display package 9 is an air-tight package, such as a sealed plastic bag or bubble pack. Package 9 prevents air from entering container 2 and activating the heater. Alternatively, seals could be place over the top and bottom air ports. Mechanical activation of the exothermic reaction in this case comprises compromising the package or seals, as the case may be.

To use the dispensing system, a user removes shipping and display package 9 and disposes dispenser 1 in a vertical attitude. Air enters the air passageway of inner container 2 through ports 3, 10 and 4, 11. In the case of the iron oxidation system, air entering the passageway contacts the reactants in packs 5 initiating an exothermic reaction. A vertical convection current results. Hot air rises, and the exothermic reaction causes air to be drawn into the heater through ports 3, 10, to pass upwardly in the air passageway through and around packs 5, where it is heated, and past volatile components 6, which are caused to evaporate, and then out of dispenser 1 through top ports 4, 11. Volatile compound or compounds 6 are heated due to the exothermic reaction in packs 5.

The shape of dispenser 1 is not critical. It could, for example, be circular, oval or rectangular in horizontal cross section. The number, pattern and size or sizes of ports 3, 10 and ports 4, 11 are adjusted to achieve the desired air flow for a particular application. Packs 5 contain particulate solids comprising or containing ingredients for the heating reaction. Reactants could as well be added as loose particles and kept in place by placing a fine screen atop them. Eyelet 8 could be replaced with a hook for hanging the dispensing system, or one portion of a hooks-and-loops fabric fastener commonly known as Velcro® (Velcro USA, Inc., Manchester, N.H., U.S.A.) or magnet or releasable glue patch or other means suitable for attaching the dispensing system to a vertical surface. Alternatively or in addition, outer package 7 could include a base (see FIG. 2) for standing the dispensing system upright on a horizontal surface such as, for example, a table top.

Figure 2:
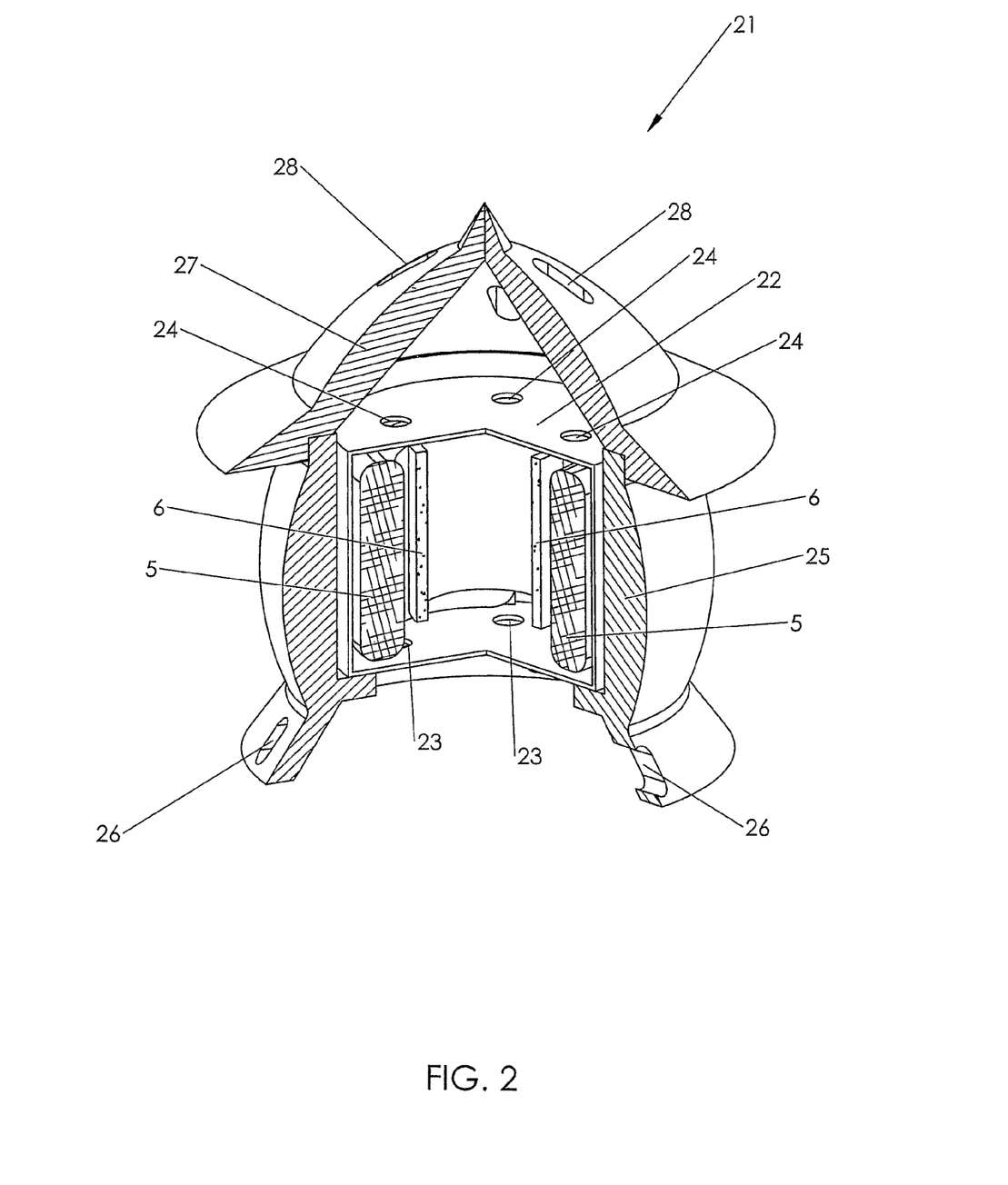
FIG. 2 is a cross-sectional view of another embodiment of a dispenser according to this invention with a separate outer package suitable both for suspending and for placing on a horizontal surface.

FIG. 2 shows in cross section a dispenser 21 comprising a decorative outer container 25 suitable for refilling with new inner containers. Inner container 22 is similar to inner container 2 (FIG. 1) except that it is removably inserted into the outer packaging. It includes bottom openings, ports 23, and top openings, ports 24 for air flow. It contains porous packs 5 and volatile compounds 6 as described above. Inner container 22 and its contents are supplied in an air-tight package, not shown (see FIG. 1), and the exothermic reaction is mechanically activated by removing the airtight package, at which time inner container 22 is placed in the outer container.

Insulated outer container 25 has a removable top 27. Top 27 could as well be a hinged openable top. Container 25 includes a base with openings for air, circumferential holes 26. Top 27 includes openings for air, a pattern of holes 28. Because there is a space between holes 26 and ports 23, alignment is not required. Similarly, because there is space between holes 28 and ports 24, alignment is not required. It will be appreciated that insulated outer container 25 could as well be adapted for hanging or attachment to a vertical surface.

In another embodiment, reusable outer container 25 could contain supports allowing packs 5 and volatile material carrier 6 to be inserted individually. These disposable components would be packaged in sealed airtight bags from which they would be removed for activation and dispensing.

Figure 3:
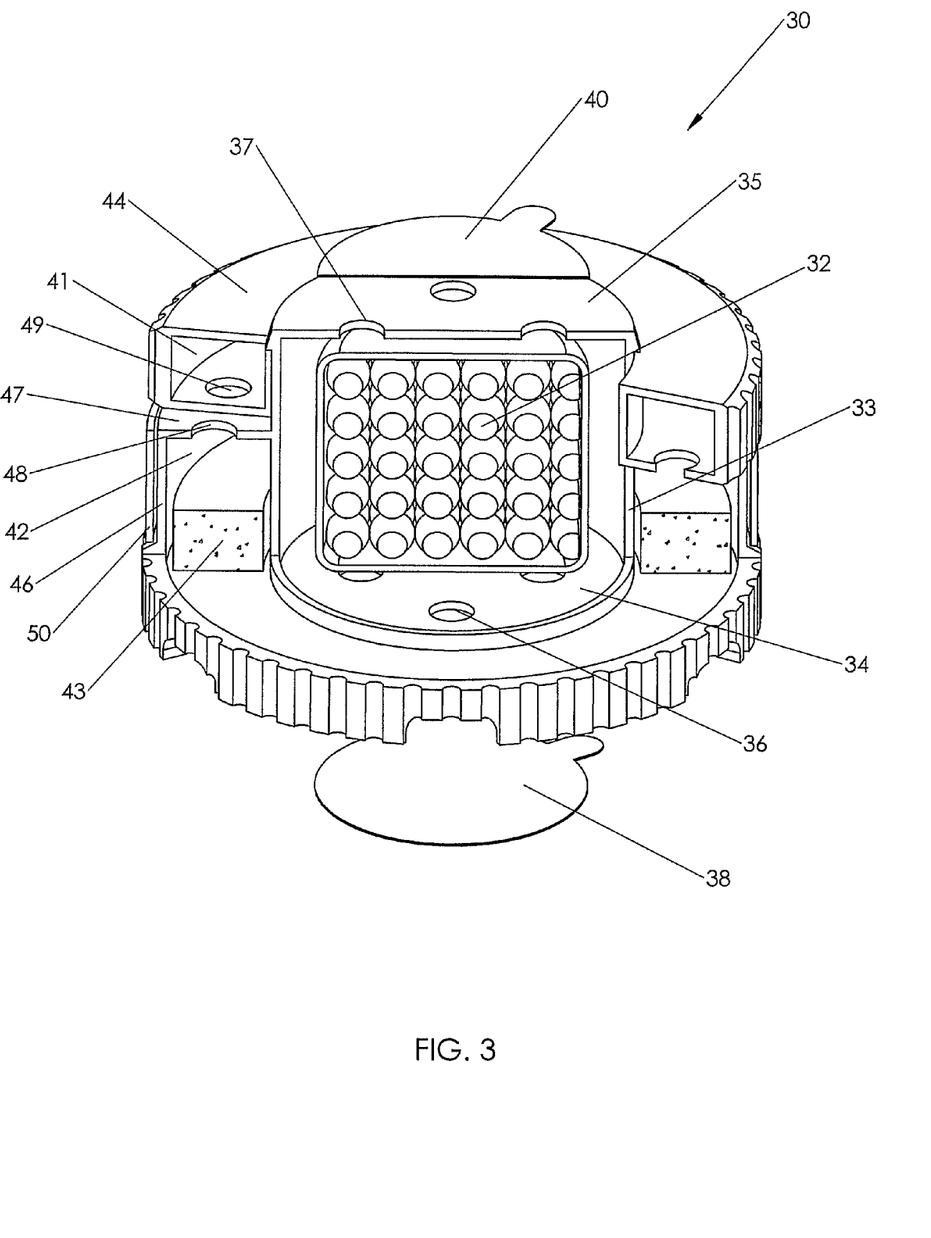
FIG. 3 is a cross-sectional view of the top of a dispenser that is activatable by twisting.

FIG. 3 shows an alternate construction providing a different type of mechanical activation that is suitable for use with air-activated heaters and for use with non-air-activated heaters, for example, oxidizer comprising solid inert pellets containing potassium permanganate particles and fuel comprising aqueous glycerin, or, alternatively, solid calcium oxide and water. For exothermic reactions utilizing a liquid reactant, such as the two last mentioned, we prefer that dispensing air not flow through the reaction zone so as to preclude leakage of liquid from the dispenser. FIG. 3 shows a dispenser 30, an insulated single-container dispenser with multiple chambers. A central cylindrical chamber containing volatile compounds 32, shown as a porous bag of mothball particles, is the air passageway. The air passageway is defined by inner cylindrical wall 33, inner bottom 34, and top 35. Inner bottom 34 and top 35 are provided with inlet ports 36 and outlet ports 37, respectively.

FIG. 3 also shows an alternate construction for a user-openable air passageway. Bottom 34 and top 35 are provided with peel-off covers 38 and 40, respectively, that block inlet ports 36 and outlet ports 37 prior to use and prevent evaporated volatile compound from exiting the dispenser through outlet ports 37. Covers 38, 40 could be replaced, of course, by an airtight container such as container 9 shown in FIG. 1.

Cylindrical wall 33 is heat-conducting, for example, metal. Dispenser 30 includes an annular heater surrounding the central chamber. The annular heater includes two vertically separated chambers, upper annular chamber 41 filled with liquid reactant (not shown) and lower annular chamber 42 containing solid reactant 43. Upper chamber 41 is defined by hollow ring 44. Lower annular chamber 42 is defined by inner cylindrical wall 33, outer cylindrical wall 46, annular top 47, and bottom 34. Rotatable annular ring 44 is rotatably attached to top 35 and slidingly engaged with inner cylindrical wall 33. Lower annular chamber 42 and rotatable hollow ring 44 are in sliding relationship. Fixed top 47 of lower annular chamber 42 is provided with inlet holes 48, and rotatable hollow ring 44 is provided with holes 49, which can be rotated into and out of alignment with holes 48 by turning rotatable ring 44 so as to enable or prevent the flow of liquid reactant into bottom chamber 42, respectively. Outer cylindrical wall 46 is insulative to protect users and reduce heat loss. If wall 46 is not sufficiently insulating from its composition and thickness, outer insulating cylinder 50, for example a polystyrene foam sleeve, may be provided Mechanical activation of the heater comprises rotating ring 44 to align holes 48, 49, thereby compromising the separation of chambers 41, 42 and permitting liquid fuel to contact the oxidizer, in this case solid oxidizer 43. Cover patches 38 and 40 are removed, thereby completing the opening of the passageway for convective airflow. As an alternative to cover patches 38 and 40 dispenser 30 could be provided in an air-tight package, in which case opening the package would remove the blockage provided by the package and open the air passageway to inflow and discharge. In special cases in which the material to be dispensed has a very low evaporative rate at room temperature, ports 36, 37 may not be blocked. Air is permitted to enter the inner chamber and contact porous bag 32 of volatile compound. Liquid reactant from chamber 41 flows by gravity into chamber 42 where it contacts solid reactant 43 and initiates an exothermic reaction. Heat from the reaction increases the temperature of air in the inner chamber, the air passageway, thereby inducing convective flow of air into inlet ports 36, around and through porous bag 32, and out discharge ports 37.

The construction of dispenser 30 could be reversed, with heater chambers 41, 42 on the inside and the volatile product 32 in an outer annular air passageway chamber. Such a construction would have the advantage that the exothermic reaction would be on the inside of cylindrical wall 33, and outer walls 44, 46 would not need to be as insulative. Central reactant chambers 41, 42 could be separated by rotatable top and bottom walls with alignable holes, similarly to the design shown in FIG. 3. Alternatively, a central upper chamber could be a liquid-filled balloon placed above solid reactant 43, in which case mechanical activation would be compromising the balloon wall separator, as by releasing a spring loaded dart by engaging a trigger located on top 35 or bottom 34. FIG. 3 illustrates a construction technique that can also be applied to a user-openable air passageway, namely, slidingly engaged rotatable elements with alignable holes. For example, if the construction of dispenser 30 were reversed as described above, with a central heater and an annular air passageway, lower chamber 42 could hold volatile compounds 32, and hollow ring 44 could be open-topped or top vented. Holes 48 would be the air passageway outlet ports, openable by rotating holes 49 into alignment with holes 48. The same approach could be employed for use with a central air passageway, as follows: if the top of hollow ring 44 were made circular rather than annular, the central portion could overlie and slidingly engage top 35 and be provided with holes that align with outlet ports 37 when holes 49 are rotated into alignment with holes 49 to initiate the exothermic reaction. Analogous constructions could be used for annular or central air passageway air inlet ports to utilize rotation to align holes and open air inlet ports. Rotatably openable air inlet ports, air outlet ports, or both are alternatives to removable cover patches or openable airtight shipping and display packages. As will be appreciated, construction of dispenser 1 (FIG. 1) could similarly be reversed with heater ingredients in the middle and surrounded by volatile compound 6. If a rotatable lower cover with alignable holes were used in an air-activated dispenser, rotation of the lower cover would simultaneously open the air passageway inlet ports and remove the separation between reactants, that is, initiate the exothermic reaction. Construction of other activation mechanisms is within the skill of the art.

The following examples illustrate heating and dispensing volatile compounds in a solid form and liquid form.

Example 1

A porous pack containing 22 g of a mixture of iron powder, carbon powder, water, non-reactive particulate absorbent (vermiculite), and sodium chloride, according to U.S. Pat. No. 3,976,049 was placed inside a vertically disposed cardboard tube 10 cm tall having a cross section of 6.4 cm wide by 2.5 cm deep. The top and bottom were open. The contents of the pack began to react with $O_2$ in the atmosphere and become heated. Thermocouples were placed at the top and bottom openings, and inside the center of the tube, near the heat pack. After 15 minutes of operation the tube adjacent the porous pack, that is, in the heating zone or in the heater, was heated to 38° C. It continued rising to 45° C. after 400 minutes, when data recording was stopped. The inlet air at the bottom opening was at 23° C. Exit air at the top increased to 25° C. over 1 hour. After 1 hour of operation the top and bottom openings were partially covered to reduce them to 1.3 cm by 2.5 cm. The exiting air temperature increased immediately to 34° C. This slowly declined to 30° C. at about 120 minutes, where it stayed until about 260 minutes, when the inlet air temperature dropped to 21° C. and the outlet air temperature correspondingly dropped to 28° C., where it remained. Data recording was stopped after 400 minutes, at which time the temperature in the heating zone was still 45° C. The prototype dispenser could operate for longer than 400 minutes.

Example 2

A second vaporizing dispenser was made with the same amount of heater ingredients divided into four porous packs. These were stacked and wrapped with foam to make a heating chamber 7.6 cm tall by 3.8 cm wide by 0.6 cm deep. The thermocouple was placed between the two middle porous packs. This simulated a dispensing system wherein the inner container 2 (FIG. 1) and the outer container 7 (FIG. 1) are combined into a single insulated container. This vaporizer heated rapidly to 57° C. and then slowly to 60° C. at 90 minutes, after which it began to drop, reaching 50° C. at 240 minutes. The temperature at the top of the tube spiked quickly to 52° C., dropped to 35° C. at 30 minutes, and then slowly descended to room temperature at about 250 minutes.

Example 3

A 0.36 g piece of filter paper was wetted with 0.46 g of a volatile compound, a scented oil removed from a commercial electrically heated dispenser. It was hung from a balance beam of a scale in a 21° C. room. The weight was recorded at intervals. The weight was divided by the initial weight of the oil to give the % remaining weight. This is shown as curve 41 in FIG. 4.

Example 4

Two porous packs containing 22 g of the mixture of iron powder, carbon powder, water, absorbent particulate, and salt described in Example 1 were placed inside a plastic box 11 cm tall with a cross section of 7 cm by 4 cm. The contents of the packs began to react with $O_2$ in the atmosphere and became heated. The box had four holes in the top and eight holes around the bottom, all of 6 mm diameter. A 0.34 g filter paper wetted with 0.46 g of the commercial scented oil described in Example 3 was hung inside the center of the box, between the two heat packs. The filter paper was removed from the heater and the weight was recorded at intervals. The weight was divided by the initial weight of the oil to give the % remaining weight. This is shown as curve 42 in FIG. 4. A thermocouple was placed inside the box against the filter paper. The recorded temperature varied between 43° C. and 58° C., depending on exactly where the thermocouple was placed after each removal of the paper for weighing.

Figure 4:
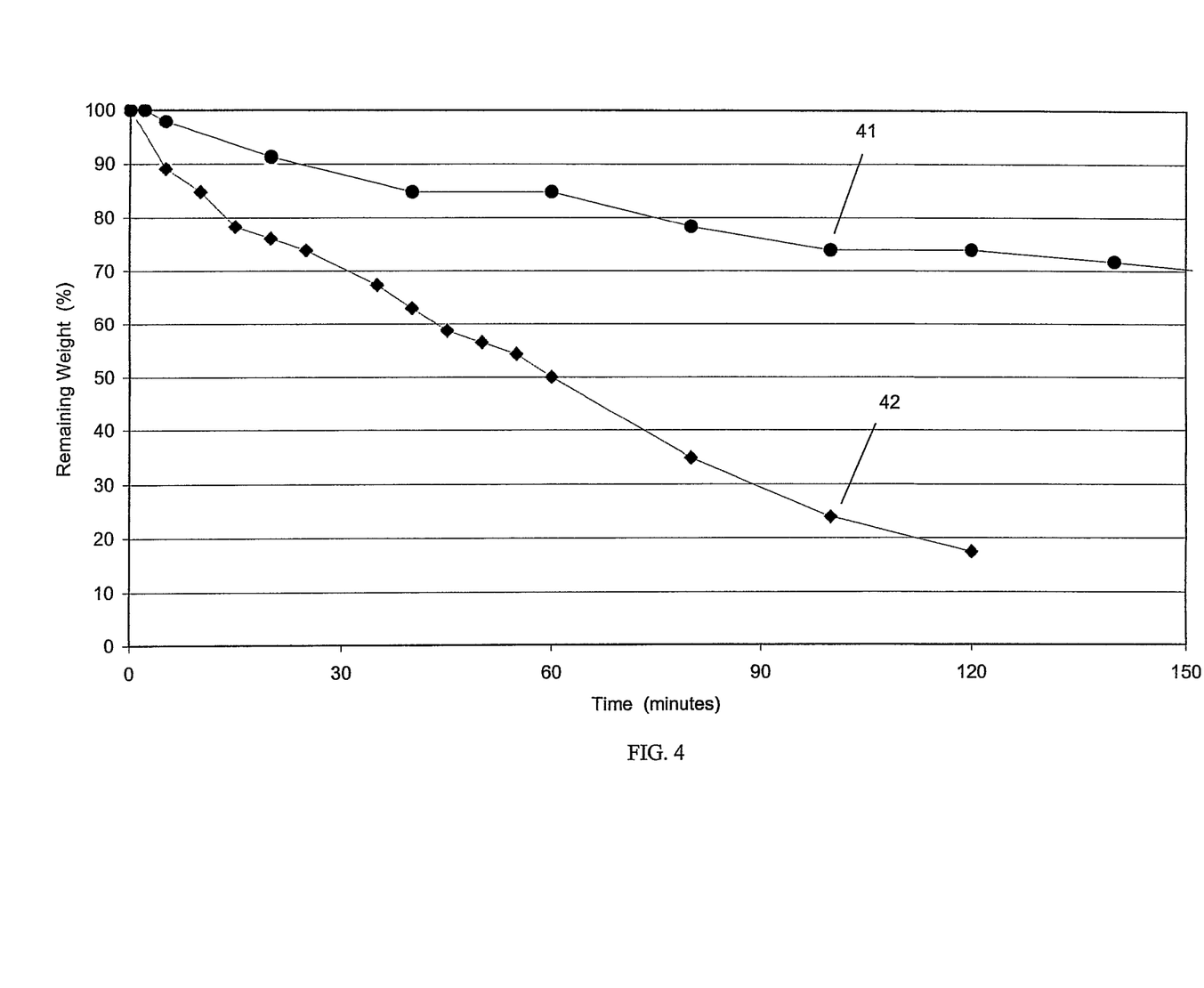
FIG. 4 and FIG. 5 are graphs showing weight loss over time of volatile compounds in dispensers according to this invention.

FIG. 4 shows that at room temperature 26% of the oil had evaporated after two hours in Example 3, while 83% of the oil had evaporated in the prototype dispenser during the same time in Example 4. This shows an approximate tripling of the evaporation rate by use of the invention. As the rate of evaporation may be adjusted by changing the temperature, any desired evaporation rate may be achieved by changing the design of the heater: adding insulation or more heating material to raise the temperature, or reducing insulation or heating material to lower the temperature or adjusting the port size of the intake and/or exit.

Example 5

A 2.81 g naphthalene (melting point approximately 80° C.) moth ball was hung on a balance in a 21° C. room. The weight was recorded at intervals. The weight was divided by the initial weight of the moth ball to give the % remaining weight. This is shown as curve 51 in FIG. 5.

Example 6

Two porous packs containing 22 g of the mixture of iron powder, carbon powder, water, particulate absorbent, and salt described in Example 1 were placed inside a plastic box 11 cm tall with a cross section of 7 cm by 4 cm. The contents of the pack began to react with $O_2$ in the atmosphere and became heated. The box had four holes in the top and eight holes around the bottom, all of 6 mm diameter. A 2.78-g naphthalene moth ball was hung inside the center of the box, between the two heat packs. The moth ball was removed from the heater and the weight was recorded at intervals. The weight was divided by the initial weight of the moth ball to give the % remaining weight. This is shown as curve 52 in FIG. 5. A thermocouple was placed inside the box against the moth ball. The recorded temperature varied between 43° C. and 54° C., depending on exactly where the thermocouple was placed after each removal of the moth ball.

Figure 5:
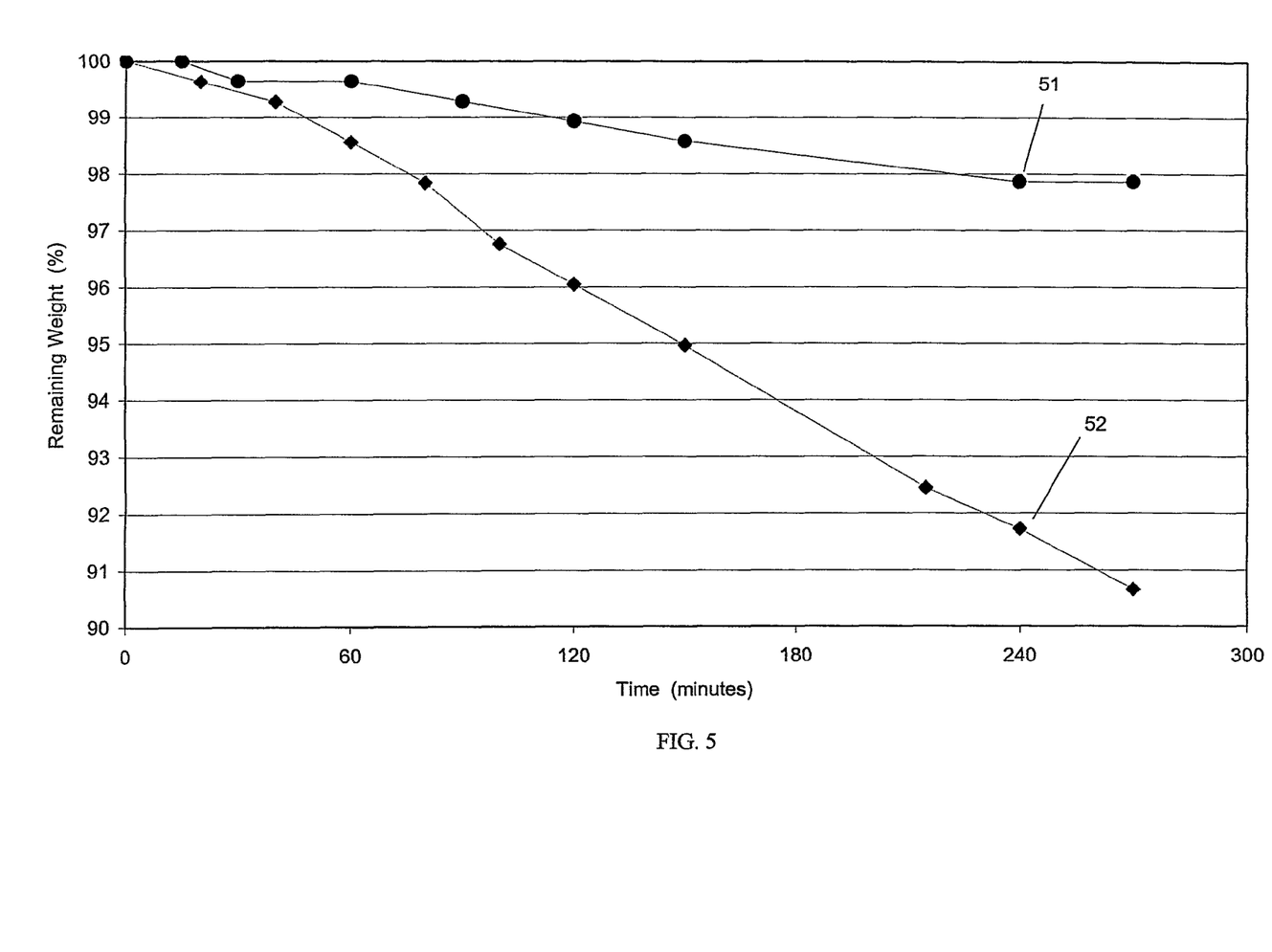

FIG. 5 shows that at room temperature 2.1% of the moth ball had evaporated after 4½ hours in Example 5, while 9.4% of the moth ball had evaporated in the heater during the same time in Example 6. This shows an approximate quadrupling of the evaporation rate by use of the invention.

A number of embodiments of the invention have been described. Nevertheless, it will be understood that various modifications may be made without departing from the spirit and scope of the invention described in the following claims

What is claimed is:

1. A convection-driven vaporizing dispenser comprising
a first container having a vertically ascending air passageway from at least one first lower air-inlet port to at least one higher air-outlet port;
residing in said first container and contactable by air in said passageway at least one volatile compound to be dispensed, said at least one volatile compound being a solid or being a liquid held in a solid;
residing in said first container in thermal contact with air in said air passageway a chemical reaction heater having a useful operating life of at least several minutes; and
physical separation means, compromisable by a user, associated with said dispenser for preventing activation of the chemical reaction heater by isolating reactants from each other,
wherein when a user compromises the physical separation means, the heater activates and wherein during use the chemical reaction heater induces convective airflow through said passageway such that air enters through said at least one bottom air-inlet port, is heated and passed over the at least one volatile compound, and
wherein heated air carrying vaporized volatile compound is dispensed through said at least one outlet port.

2. The vaporizing dispenser according to claim 1 wherein said at least one air-inlet port and said at least one air-outlet port are blocked by at least one user-openable blockage associated with the dispenser.

3. The vaporizing dispenser according to claim 2 wherein the at least one user-openable blockage is selected from the group consisting of an airtight package containing said first container, removable sealing patches covering said ports, and a rotatable second outer lower section containing at least one hole alignable with said at least one air inlet port.

4. The vaporizing dispenser according to claim 2 wherein one of said exothermic reactants is oxygen supplied by ambient air and wherein said at least one blockage comprises said physical separation means.

5. The vaporizing dispenser according to claim 4 wherein the at least one user-openable blockage is an airtight package containing said first container.

6. The vaporizing dispenser according to claim 2 wherein the chemical reaction heater comprises a first liquid reactant in a first compartment in the first container and a second liquid or solid reactant in a second compartment in the first container, and wherein the user-compromisable separation means prevents said first liquid reactant from flowing into said second compartment.

7. The vaporizing dispenser according to claim 6 wherein said first and second compartments are physically isolated from said air passageway.

8. The vaporizing dispenser according to claim 6 wherein said separator comprises at least one pair of offset holes that can be moved into alignment to create a liquid flow path across said separator.

9. The vaporizing dispenser according to claim 6 wherein said first compartment comprises a balloon in said second compartment, and wherein said dispenser includes a spring-loaded dart releasable by a user to puncture said balloon.

10. The vaporizing dispenser according to claim 1 wherein the chemical reaction heater comprises a first liquid reactant in a first compartment in the first container and a second liquid or solid reactant in a second compartment in the first container, and wherein the user-compromisable separation means prevents said first liquid reactant from flowing into said second compartment.

11. The vaporizing dispenser according to claim 10 wherein said first and second compartments are physically isolated from said air passageway.

12. The vaporizing dispenser according to claim 1 wherein the chemical reaction heater has a useful operating life of at least two hours.

13. The vaporizing dispenser according to claim 1 having insulation surrounding said first container.

14. The vaporizing dispenser according to claim 1 including an outer second container that includes at least one bottom opening permitting air to enter said air-inlet port and at least one top opening permitting air from said air-outlet port to exit the dispenser.

15. The vaporizing dispenser according to claim 14 wherein the outer second container is integral with said first container.

16. The vaporizing dispenser according to claim 15, wherein one of said exothermic reactants is oxygen supplied by ambient air, wherein said at least one bottom opening and said at least one top opening are blocked by at least one user-openable blockage that prevents air from entering said air-inlet and air-outlet ports, and wherein said at least one blockage comprises said physical separation means.

17. The vaporizing dispenser according to claim 16, wherein the second container includes insulation that insulates the first container.

18. The vaporizing dispenser according to claim 14 wherein the first container is removably insertable into the second container.

* * * * *